(12) United States Patent
McClintock

(10) Patent No.: US 8,449,554 B2
(45) Date of Patent: May 28, 2013

(54) INTERVERTEBRAL IMPLANT AND INSTRUMENT WITH REMOVABLE SECTION

(75) Inventor: Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 560 days.

(21) Appl. No.: 12/398,316

(22) Filed: Mar. 5, 2009

(65) Prior Publication Data

US 2009/0228110 A1    Sep. 10, 2009

Related U.S. Application Data

(60) Provisional application No. 61/068,564, filed on Mar. 7, 2008.

(51) Int. Cl.
*A61B 17/70* (2006.01)

(52) U.S. Cl.
USPC .............................. 606/99; 606/86 A; 606/90

(58) Field of Classification Search
USPC ............................................ 606/86 A, 90, 99
See application file for complete search history.

(56) References Cited

U.S. PATENT DOCUMENTS

| | | | |
|---|---|---|---|
| 5,431,658 A | | 7/1995 | Moskovich |
| 5,599,279 A * | | 2/1997 | Slotman et al. ............... 600/201 |
| 6,569,168 B2 | | 5/2003 | Lin |
| 6,770,074 B2 | | 8/2004 | Michelson |
| 6,986,772 B2 | | 1/2006 | Michelson |
| 7,070,598 B2 | | 7/2006 | Lim et al. |
| 7,087,055 B2 | | 8/2006 | Lim et al. |
| 7,445,637 B2 | | 11/2008 | Taylor |
| 1,476,252 A1 | | 1/2009 | Foley |
| 7,473,256 B2 | | 1/2009 | Assell et al. |
| 7,481,812 B2 | | 1/2009 | Frey et al. |
| 7,485,120 B2 | | 2/2009 | Ray |
| 8,016,829 B2 * | | 9/2011 | Mahoney et al. ........... 606/86 A |
| 2003/0149438 A1 | | 8/2003 | Nichols et al. |
| 2003/0195520 A1 * | | 10/2003 | Boyd et al. ...................... 606/90 |
| 2004/0002758 A1 | | 1/2004 | Landry et al. |
| 2004/0024408 A1 * | | 2/2004 | Burkus et al. ................... 606/90 |
| 2004/0172037 A1 * | | 9/2004 | Dorchak et al. ................ 606/90 |
| 2004/0267277 A1 | | 12/2004 | Zannis et al. |
| 2005/0021042 A1 | | 1/2005 | Marnay et al. |
| 2005/0113842 A1 * | | 5/2005 | Bertagnoli et al. ............. 606/90 |
| 2005/0165408 A1 | | 7/2005 | Puno et al. |
| 2005/0182416 A1 | | 8/2005 | Lim et al. |
| 2006/0030856 A1 | | 2/2006 | Drewry et al. |
| 2006/0030857 A1 * | | 2/2006 | de Villiers et al. .............. 606/90 |
| 2006/0030862 A1 | | 2/2006 | De Villiers et al. |
| 2006/0052793 A1 * | | 3/2006 | Heinz ............................. 606/90 |
| 2006/0064107 A1 | | 3/2006 | Bertagnoli et al. |
| 2006/0095043 A1 * | | 5/2006 | Martz et al. ..................... 606/90 |

(Continued)

*Primary Examiner* — David Isabella
*Assistant Examiner* — Randy Shay
(74) *Attorney, Agent, or Firm* — Carter, DeLuca, Farrell & Schmidt, LLP

(57) ABSTRACT

An intervertebral instrument includes a shaft having distal and proximal ends. The proximal end of the shaft includes an attaching feature connected to handle. The shaft defines a pair tracks disposed along a portion of the surface thereof. The distal end includes a pair of wings. Each track guides instruments and implants along the intervertebral instrument. The implants are configured to receive bone graft or bone enhancers. The distal end of the shaft may include a removably attachable tip configured to engage the implants. The implants and the removably attachable tip form an implantable intervertebral disk. An intervertebral instrument and implant kit is also disclosed. A method of inserting intervertebral implants is also disclosed.

16 Claims, 7 Drawing Sheets

U.S. PATENT DOCUMENTS

| | | |
|---|---|---|
| 2006/0149284 A1 | 7/2006 | McCormack et al. |
| 2006/0167461 A1 | 7/2006 | Hawkins et al. |
| 2006/0235423 A1 | 10/2006 | Cantu |
| 2006/0241641 A1 | 10/2006 | Albans et al. |
| 2006/0241643 A1 | 10/2006 | Lim et al. |
| 2007/0016220 A1 | 1/2007 | Michelson |
| 2007/0016221 A1 | 1/2007 | Beyersdorff et al. |
| 2007/0123901 A1 | 5/2007 | Foley et al. |
| 2007/0123903 A1 | 5/2007 | Raymond et al. |
| 2007/0123904 A1 | 5/2007 | Stad et al. |
| 2007/0191857 A1 | 8/2007 | Allard et al. |
| 2007/0198025 A1 | 8/2007 | Trieu et al. |
| 2007/0233143 A1 | 10/2007 | Josse et al. |
| 2007/0260315 A1 | 11/2007 | Foley et al. |
| 2007/0270873 A1 | 11/2007 | Flickinger et al. |
| 2008/0077153 A1 | 3/2008 | Pernsteiner et al. |
| 2008/0114367 A1 | 5/2008 | Meyer |
| 2008/0161817 A1 | 7/2008 | Parsons et al. |
| 2008/0177275 A1 | 7/2008 | Wing et al. |

* cited by examiner

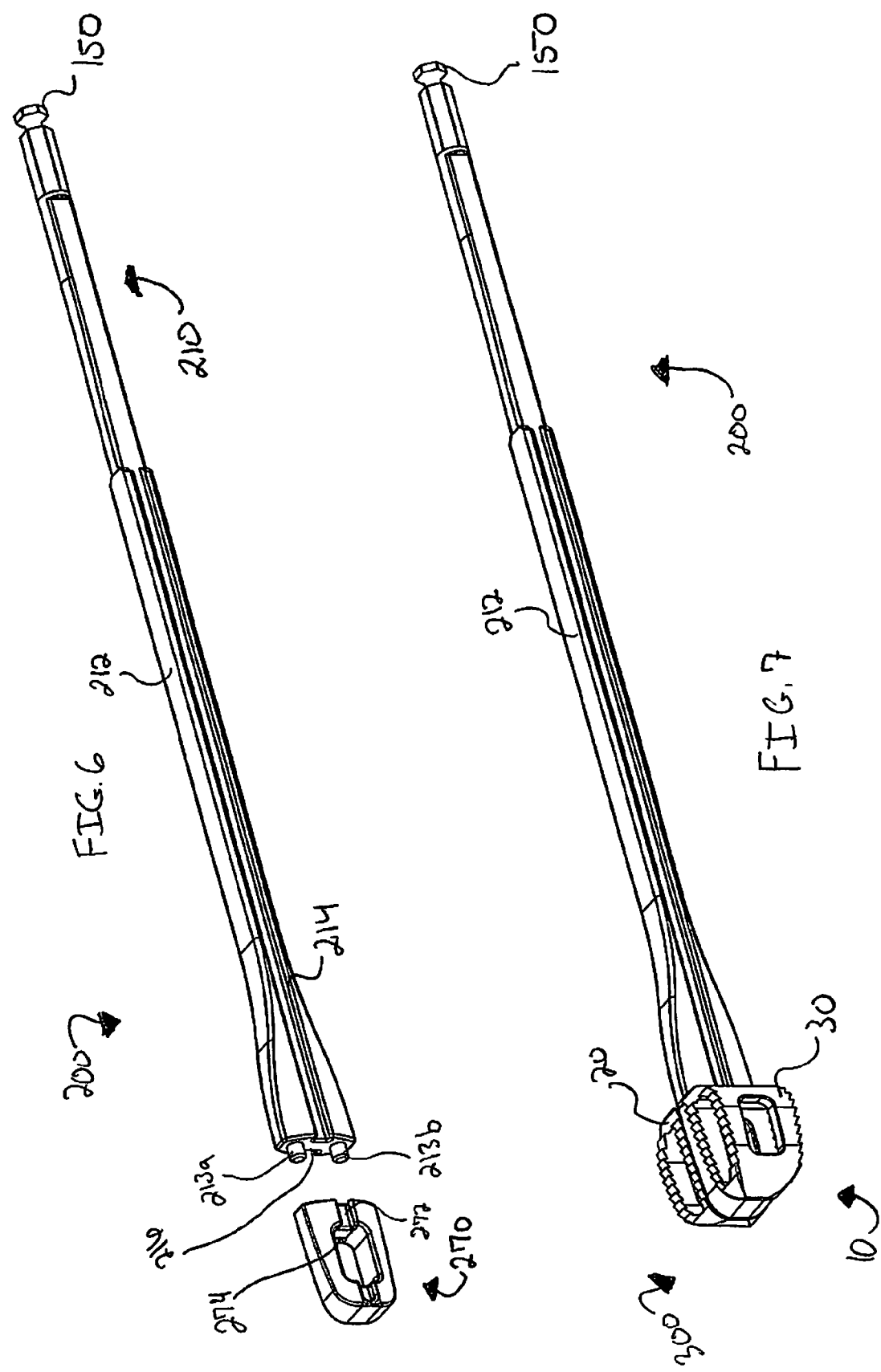

INTERVERTEBRAL IMPLANT AND INSTRUMENT WITH REMOVABLE SECTION

CROSS-REFERENCE TO RELATED APPLICATIONS

This application claims the benefit of, and priority, to U.S. Provisional Patent Application Ser. No. 61/068,564, filed Mar. 7, 2008, the entire contents of which are incorporated by reference herein.

BACKGROUND

1. Technical Field

This application relates to intervertebral distracting instruments, intervertebral disc implants, and a method for inserting intervertebral disc implants between affected vertebrae to achieve spinal fusion.

2. Background of Related Art

The human spine is composed of thirty-three vertebrae at birth and twenty-four as a mature adult. Between each pair of vertebrae is an intervertebral disc, which maintains the space between adjacent vertebrae and acts as a cushion under compressive, bending, and rotational loads and motions. A healthy intervertebral disc has a great deal of water in the nucleus pulposus, which is the center portion of the disc. The water content gives the nucleus a spongy quality and allows it to absorb spinal stress. Excessive pressure or injuries to the nucleus can cause injury to the annulus, which is the outer ring that holds the disc together. Generally, the annulus is the first portion of the disc that experiences injury. These injuries are typically in the form of small tears. These tears heal by scar tissue. The scar tissue is not as strong as normal annulus tissue. Over time, as more scar tissue forms, the annulus becomes weaker. Eventually this can lead to damage of the nucleus pulposus. The nucleus begins to lose its water content due to the damage, i.e., it begins to dry up. Because of water loss, discs lose some of their ability to act as a cushion. This can lead to even more stress on the annulus and still more tears as the cycle repeats. As the nucleus loses its water content it collapses, allowing the vertebrae above and below the disc space to move closer to one another. This results in a narrowing of the disc space between the two vertebrae. As this shift occurs, the facet joints located at the back of the spine are forced to shift. This shift changes the way the facet joints work together, and thus, can cause problems in the facet joints as well.

When a disc or vertebra is damaged due to disease or injury, standard practice is to remove all or part of the intervertebral disc, insert a natural or artificial disc spacer, and construct an artificial structure to hold the affected vertebrae in place to achieve a spinal fusion. The procedure may be accomplished using various approaches such as anteriorly, posteriorly and transforaminally. Depending on which approach is used, a specific geometry spacer device is selected.

Anteriorly approached procedures are preferred when one of the clinician's goals is to use a spacer device that most closely matches the footprint of the vertebral body. This maximum sized footprint also allows for the introduction of a significant amount of bone graft. It may also promote a better bone fusion. The preferred instrument to introduce an anterior spacer device is a "sled" style instrument. The sled provides the necessary vertebral body distraction and a path for introducing the device. Unfortunately, the sleds currently available are very bulky, complicated to use, and obstruct the clinician's working view.

For the above stated reasons, a need exists for a system that includes an instrument for distracting the vertebral bodies in such a way that does not obstruct the surgeon's view and still allows additional disc space work to be performed. The system must also provide a pathway for introducing the device into the intervertebral disc's space.

SUMMARY

The present disclosure relates to an intervertebral instrument including a shaft having distal and proximal ends. The proximal end of the shaft includes an attaching feature for enabling the shaft to attach to a handle for manipulating the shaft. The shaft defines at least one track at least partially disposed along a portion of the surface thereof. The distal end of the shaft includes a pair of wings for distracting an intervertebral disk space defined between two vertebrae. Each track is configured and dimensioned to guide instruments and intervertebral implants used in intervertebral procedures toward the intervertebral disk space. The intervertebral instrument is configured and dimensioned to be utilized with a plurality of different sized patients.

In another embodiment of the intervertebral instrument, the distal end of the shaft includes a removably attachable tip configured and dimensioned to engage the implants. The removably attachable tip is configured and dimensioned to keep implants affixed thereto. The intervertebral implants and the removably attachable tip are configured and dimensioned to collectively function as an implantable intervertebral disk. The implantable intervertebral disk is configured and dimensioned to receive bone graft or bone enhancers to enable bone ingrowth.

The intervertebral implants include a pair of members. The members each have a body with top, bottom, inside, and outside surfaces. The top and bottom surfaces include ridges disposed thereon. The inside surface has at least one protuberance configured and dimensioned to engage the intervertebral instrument. At least one of the members includes at least one passage for receiving bone graft or bone enhancers to enable bone ingrowth. As such, at least one of the members is configured and dimensioned to receive bone graft or bone enhancers to enable bone ingrowth.

In one embodiment, the intervertebral implant includes a removably attachable portion configured and dimensioned to connect each member. The removably attachable portion includes a pair of tracks. Each track is configured and dimensioned to engage the at least one protuberance of each member. Each member is configured and dimensioned to remain affixed to the removably attachable portion. The combination of each member and the removably attachable portion collectively function as an implantable intervertebral disk when the removably attachable portion and each member are collectively detached from the intervertebral instrument.

An intervertebral instrument and intervertebral implant kit is also envisioned and includes an intervertebral instrument and at least one intervertebral implant in accordance with the present disclosure. The kit can also include a handle disposed at the proximal end of the shaft for manipulation of the shaft. In another embodiment of the kit, the shaft includes a removably attachable tip disposed at the distal end thereof. In this embodiment of the intervertebral instrument and intervertebral implant kit, the removably attachable tip and the at least one intervertebral implant are configured and dimensioned to collectively function as an implantable intervertebral disk.

One aspect of the present disclosure contemplates a method for inserting an intervertebral implant including the steps of inserting an intervertebral instrument into the intervertebral disk space, advancing an intervertebral implant along a track toward the intervertebral disk space, inserting the implant and a removably attachable tip in the intervertebral disk space, and selectively applying bone graft or bone enhancers into the intervertebral disk space for bone ingrowth. The step of inserting the intervertebral instrument can be performed using an anterior, a posterior, a lateral, or a transforaminal approach. During the process, a user can selectively pass complementary instruments down the at least one track for facilitating the insertion of the at least one implant and any removably attachable tip attached thereto.

BRIEF DESCRIPTION OF THE DRAWINGS

The above and other aspects, features, and advantages of the present disclosure will become more apparent in light of the following detailed description when taken in conjunction with the accompanying drawings in which:

FIG. 6 is a perspective view, with parts separated, of another embodiment of the intervertebral instrument in accordance with the present disclosure;

FIG. 7 is a perspective view of the intervertebral instrument of FIG. 6 having the one member of FIG. 1 of the two identical members of the intervertebral implant attached on one side of the distal end thereof and the second member of the two identical members of the intervertebral implant attached on the other side of the distal end thereof.

DETAILED DESCRIPTION OF EMBODIMENTS

Figure 1:
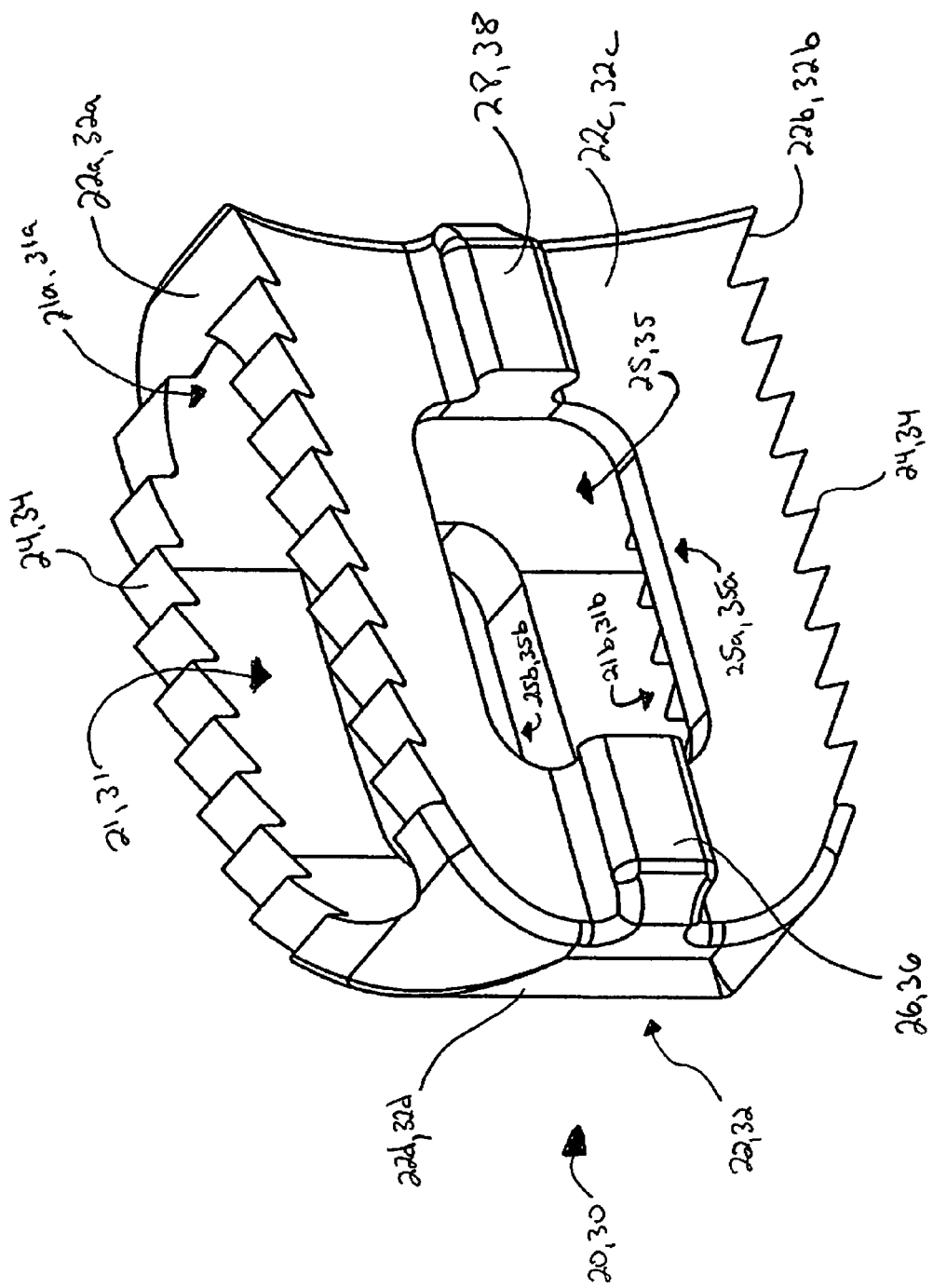
FIG. 1 is a perspective view of one of two identical members of an intervertebral implant in accordance with the present disclosure.

Various embodiments of the present disclosure will now be described in detail with reference to the drawings, wherein like reference numerals identify similar or identical elements. In the drawings and in the description that follows, the term "proximal," will refer to the end is closest to the operator, while the term "distal" will refer to the end that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 2:
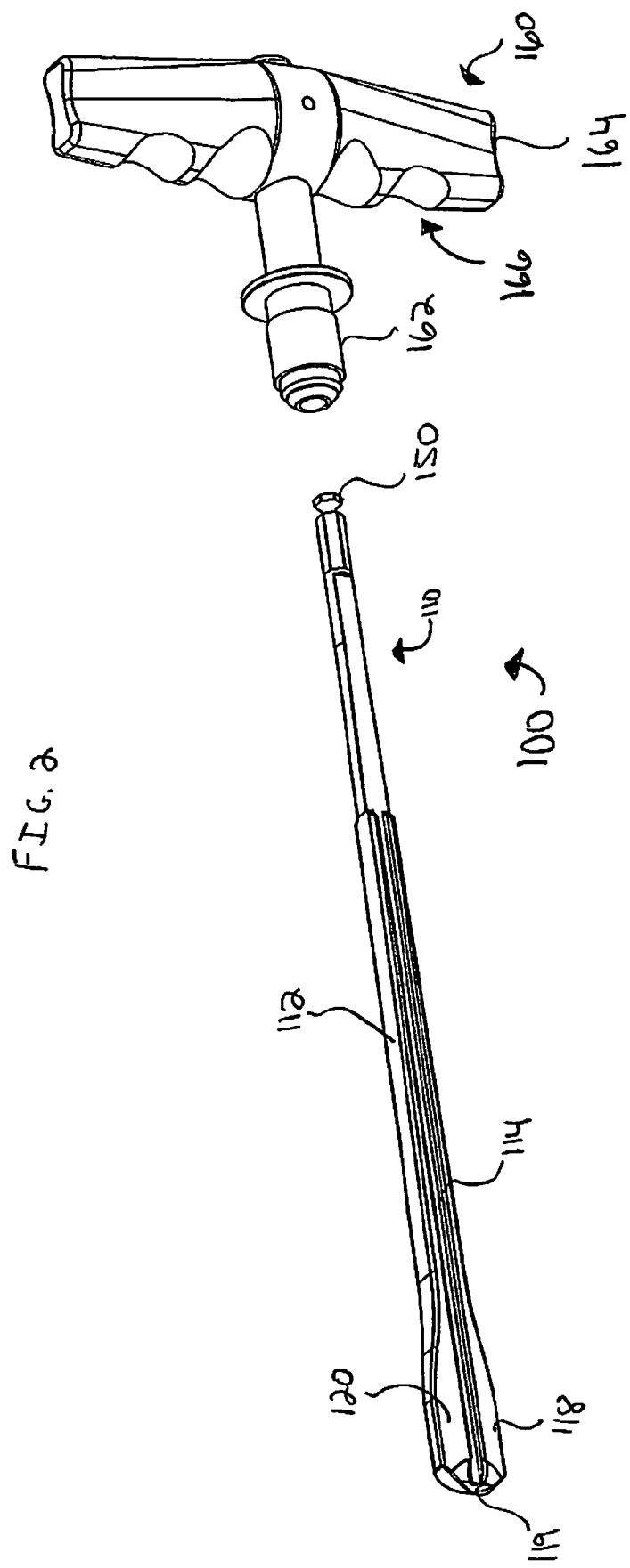
FIG. 2 is a perspective view, with parts separated, of one embodiment of the intervertebral instrument including a handle connected to the proximal end in accordance with the present disclosure.
Figure 5:
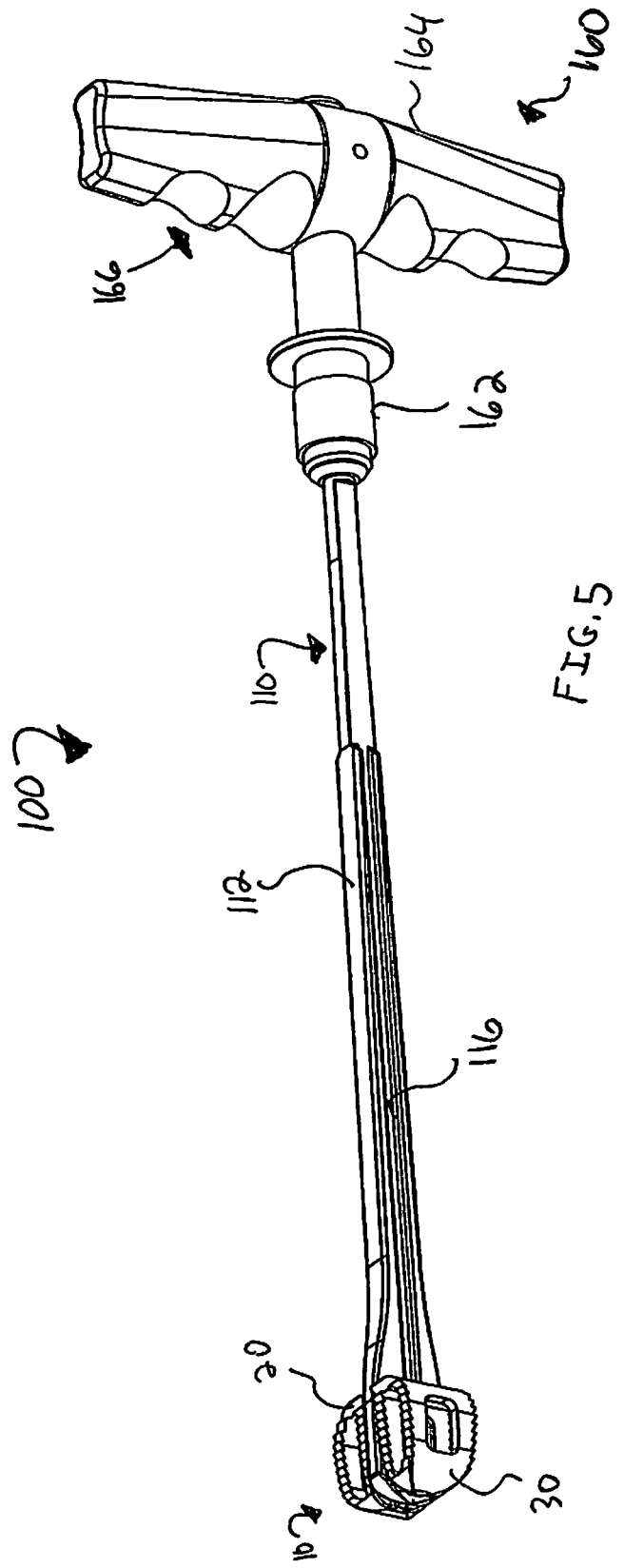
FIG. 5 is a perspective view of the intervertebral instrument of FIGS. 2-4 having the one member of FIG. 1 of the two identical members of the intervertebral implant attached on one side of the distal end thereof and the second member of the two identical members of the intervertebral implant attached on the other side of the distal end thereof, the intervertebral instrument including a handle connected to the proximal end thereof.

Referring now to the drawings, in which like reference numerals identify identical or substantially similar parts throughout the several views, FIG. 1 illustrates one portion of two identical portions of an intervertebral implant 10 (both portions shown in FIG. 5). In accordance with the present disclosure, the intervertebral implant 10 includes first and second members 20, 30. Each member 20, 30 has a body 22, 32 with a top surface 22a, 32a, a bottom surface 22b, 32b, an inside surface 22c, 32c, and an outside surface 22d, 32d. The top surface 22a, 32a and the bottom surface 22b, 32b include ridges 24, 34 disposed thereon. The inside surface 22c, 32c has a first protuberance 26, 36 distally disposed thereon and a second protuberance 28, 38 proximally disposed thereon. Each protuberance 26, 28, 36, 38 is configured and dimensioned to engage an intervertebral instrument 100, 200 (FIGS. 2 and 6). Each member 20, 30 has a channel 25, 35 cut therethrough. Each channel 25, 35 extends from a respective first opening 25a, 35a disposed on each respective inside surface 22c, 32c, to a respective second opening 25b, 35b disposed on each respective outside surface 22d, 32d. In addition, a longitudinal passage 21, 31 extends through each respective member 20, 30 from a respective first aperture 21a, 31a disposed on the respective top surface 22a, 32a to a respective second aperture 21b, 31b disposed on the respective bottom surface 22b, 32b. Each channel 25, 35 and each longitudinal passage 21, 31 are configured and dimensioned to receive bone graft or bone enhancers to enable bone ingrowth.

Referring to FIGS. 2-5, an intervertebral instrument 100 includes a shaft 110 having distal and proximal ends and an attaching feature 150. The shaft 110 includes a sleeve 112 defining a first track 114 (FIG. 2) and a second track 116 (FIG. 5) extending longitudinally along a portion of opposing external surfaces of the shaft 110. Each track 114, 116 is configured and dimensioned to guide instruments used in intervertebral procedures, such as the first instrument 80 shown in FIG. 3 or the second instrument 90 shown in FIG. 4 (each of which is described below), as well as the respective members 20, 30 of implants 10 toward the intervertebral disk space. The distal end of the sleeve 112 includes a pair of wings 118, 120 orthogonally disposed relative to first and second track 114, 116. The wings 118, 120 interconnect with each other by a contoured distal groove 119. The pair of wings 118, 120 are configured and dimensioned to distract an intervertebral disk space defined between two vertebrae.

Referring additionally to FIGS. 2 and 5, a handle 160 is removably attachable to the attaching feature 150 at the proximal end of the shaft 110. The handle 160 includes a connector 162 centrally attached to an actuator 164 at the proximal end of the connector 162. The actuator 164 includes grips 166 for engagement by a user's hand. The connector 164 is configured and dimensioned to distally and removably connect to the attaching feature 150 about the proximal end of the attaching feature 150. As such, the handle 160 is configured and dimensioned to enable the shaft 110 to be manipulated.

Figure 3:
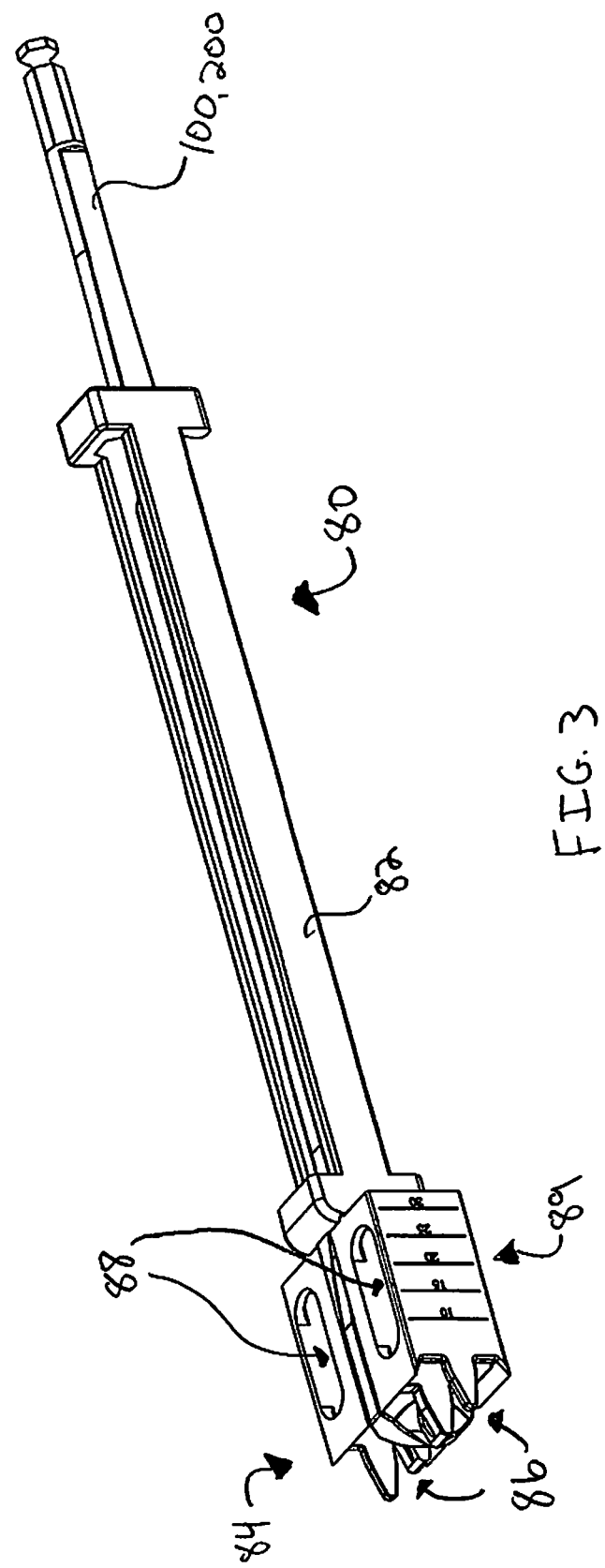
FIG. 3 is a perspective view of the intervertebral instrument of FIG. 2 (without the handle) including one embodiment of a complementary instrument attached thereto.
Figure 8:
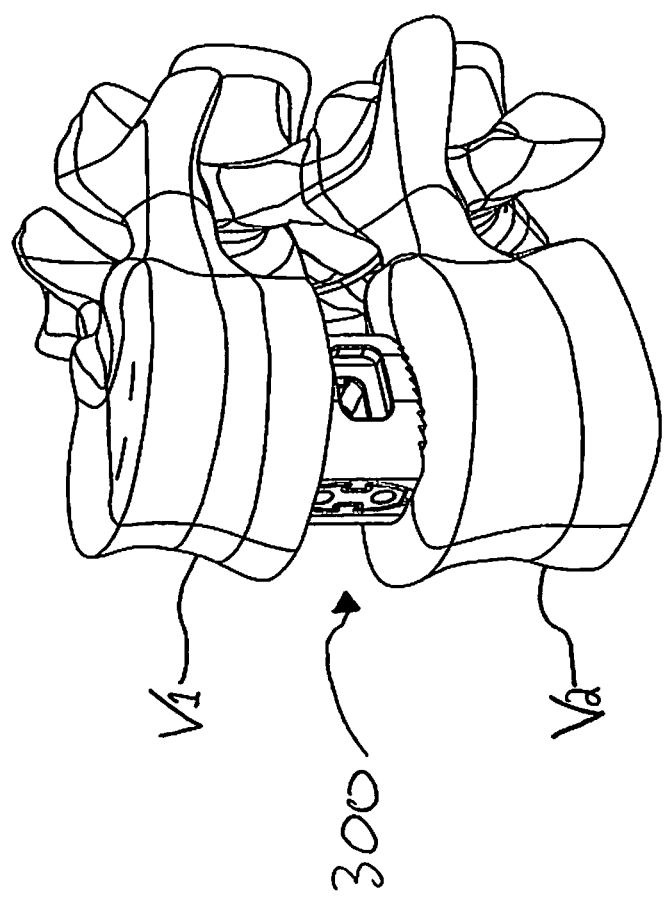
FIG. 8 is a perspective view of a fusion implant disposed between two adjacent vertebrae in accordance with the present disclosure.

Referring now to FIG. 3 the first instrument 80 includes a shaft 82 and a distracting tip 84. The shaft 82 is configured and dimensioned to engage the sleeve 112, 212 of each of the intervertebral instruments 100, 200 (FIGS. 2 and 6) so that the distracting tip 84 can be positioned within the intervertebral disk space in order to further facilitate the distraction of adjacent vertebrae "V1" and "V2" (FIG. 8). The distracting tip further includes pointed heads 86 disposed at the distal end thereof, at least one cavity 88 disposed in the body thereof for receiving members 20, 30, and a measuring guide 89 disposed on the external surface of the body thereof for measuring the placement of members 20, 30.

Figure 4:
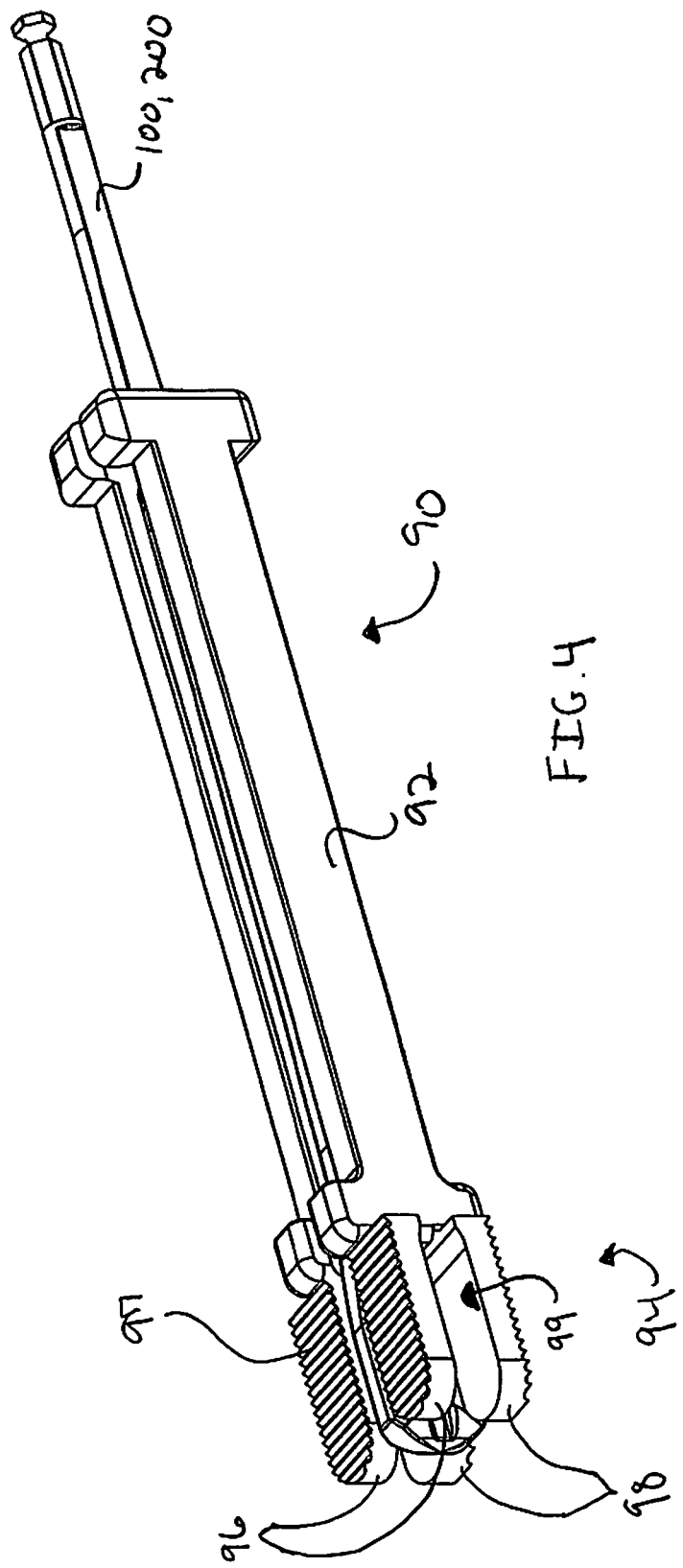
FIG. 4 is a perspective view of the intervertebral instrument of FIG. 2 (without the handle) including another embodiment of a complementary instrument attached thereto.

Referring now to FIG. 4 the second instrument 90 includes a shaft 92 and a distracting tip 94. The shaft 92 is configured and dimensioned to engage the sleeve 112, 212 of each of the intervertebral instruments 100, 200 (FIGS. 2 and 6) so that the distracting tip 94 can be positioned within the intervertebral disk space in order to further facilitate the distraction of adjacent vertebrae "V1" and "V2" (FIG. 8). The distracting tip further includes a top platform 96 and a bottom platform 98, each platform 96, 98 including ridges 97 for engaging vertebrae "V1" and "V2." Each platform 96, 98 is separated by a space 99 for receiving members 20, 30.

In a second embodiment of the intervertebral instrument, as illustrated in FIGS. 6 and 7, the intervertebral instrument 200 is substantially similar to the intervertebral instrument 100. However, the intervertebral instrument 200 includes a shaft 210 with tracks 214, 216 and a removably attachable tip 270 at the distal end thereof. The removably attachable tip 270 removably attaches to the distal end of the sleeve 212 of the intervertebral instrument 200 by a pair of stems 213a, 213b. The removably attachable tip 270 is configured and dimensioned to engage the members 20, 30 of the implant 10. A pair of tracks 272, 274 is partially longitudinally defined along opposing external surfaces of the removably attachable tip 270. The tracks 272, 274 are configured and dimensioned to guide the implants 10 (FIG. 7) and their respective members 20, 30 thereon. The removably attachable tip 270 is configured and dimensioned to keep the implants 10 affixed thereto. The removably attachable tip 270 is configured and dimensioned to engage each protuberance 26, 28, 36, 38 of each respective member 20, 30 (FIG. 1). As illustrated in FIG. 8, the intervertebral implant 10 and the removably attachable tip 270 are configured and dimensioned to collectively function as a unitary fusion implant 300 when the removably attachable tip 270 and each member 20, 30 are collectively detached from the intervertebral instrument 200. The fusion implant 300 is configured and dimensioned to remain implanted in the intervertebral disc space, i.e., between adjacent vertebrae V.

It is contemplated and within the scope of the present disclosure that the intervertebral instruments 100, 200, implants 10, and implantable intervertebral disks 300 may be used during procedures performed anteriorly, posteriorly, laterally, and transforaminally. For example, using an anterior approach, minimal disc space preparation is performed and the intervertebral instrument 100, 200 is inserted into the disc space, preferably on its midline. The intervertebral instrument 100, 200 is rotated approximately 90 degrees engaging the endplates and separating them by the height of the instrument. Several sized intervertebral instruments 100, 200 are contemplated to allow for the variations between patients. Additional, complimentary instruments 80, 90 may be passed down the tracks 114, 116, 214, 216 to prepare the disc space for the implant 10, or the implantable intervertebral disk 300. Additional complimentary instruments include, but are not limited to, box chisels, scrapers and trial implants. When the final intervertebral implants have been appropriately sized, the final intervertebral implants may be packed with bone graft and passed down the tracks 114, 116, 214, 216 of the corresponding intervertebral instrument 100, 200. After final placement of the intervertebral implant 10, or the implantable intervertebral disk 300 has been achieved, the intervertebral instrument 100, 200 may be removed and the subsequent void may be filled with additional bone graft, potentially more than with a typical anterior approach implant.

Specifically with respect to intervertebral instrument 200, the removably attachable tip 270 is made of an implant grade material, preferably PEEK. In doing so, the members 20, 30 are passed down the intervertebral instrument 200 so that they may engage and lock to the removably attachable tip 270. As such, when the intervertebral instrument 200 is removed, the implantable intervertebral disk 300 becomes a one-piece design and the removably attachable tip 270 and the members 20, 30 collectively remain in the disc space as a unitary implant 300. This design provides increased strength.

Each of these intervertebral instruments 100, 200 are configured and dimensioned to be used with a plurality of different sized patients.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

For example, it is within the scope of the present disclosure that members 20, 30 may be uniform unit without the removably attachable tip 270, i.e. a single piece intervertebral implant.

What is claimed is:

1. An intervertebral instrument and implant kit comprising:
an intervertebral instrument including a shaft having distal and proximal ends, the shaft defining at least one track at least partially disposed along a portion of the surface thereof, the distal end of the shaft including a removable section that is removable from the shaft, the removable section being configured and dimensioned to distract an intervertebral disk space defined between two vertebrae, the at least one track being configured and dimensioned to guide instruments and intervertebral implants used in intervertebral procedures toward the intervertebral disk space; and
at least one intervertebral implant selectively secured to the removable section of the shaft and including a pair of members, each member having a body with top, bottom, inside, and outside surfaces, the top and bottom surfaces including ridges disposed thereon, the inside surface having at least one protuberance, the at least one protuberance configured and dimensioned to engage the intervertebral instrument, wherein at least one of the members is configured and dimensioned to receive bone graft or bone enhancers to enable bone ingrowth.

2. The intervertebral instrument and implant kit according to claim 1, further comprising a handle disposed at the proximal end of the shaft for manipulation of the shaft.

3. The intervertebral instrument and implant kit according to claim 1, wherein the at least one intervertebral implant and the removable section of the shaft are collectively and selectively removable from the shaft.

4. The intervertebral instrument and implant kit according to claim 3, wherein the removable section of the shaft and the at least one intervertebral implant collectively define an implantable intervertebral disk that is separable from the intervertebral instrument for implantation within a patient.

5. The intervertebral instrument and implant kit according to claim 1, wherein the removable section of the shaft includes a pair of wings for distracting the intervertebral disk space.

6. An intervertebral instrument and implant kit comprising:
an intervertebral instrument including a shaft having distal and proximal ends, the shaft defining a track at least partially disposed along a portion of the surface thereof, the distal end including a removable section that is removable from the shaft and is positionable within an intervertebral disk space defined between two vertebrae to distract the two vertebrae, the track guiding instruments and intervertebral implants used in intervertebral procedures toward the intervertebral disk space; and
an intervertebral implant selectively secured to the removable section of the shaft and including a pair of members, each member having a body with top, bottom, inside, and outside surfaces, the top and bottom surfaces including ridges disposed thereon, the inside surface having a protuberance, the protuberance securable to the intervertebral instrument.

7. The intervertebral instrument and implant kit according to claim 6, wherein the intervertebral implant and the removable section of the shaft are collectively separable from the intervertebral instrument for implantation within a patient.

8. The intervertebral instrument and implant kit of claim 6, wherein at least one of the members defines at least one opening for the reception of bone graft or bone enhancers to enable bone ingrowth.

9. The intervertebral instrument and implant kit according to claim 6, further comprising a handle disposed at the proximal end of the shaft for manipulation of the shaft.

10. The intervertebral instrument and implant kit according to claim 6, wherein the removable section of the shaft includes a pair of wings for distracting the intervertebral disk space.

11. An intervertebral instrument and implant kit comprising:
an intervertebral instrument including a shaft, the shaft defining a pair of tracks at least partially disposed along a portion of opposite sides of the shaft, the tracks providing a guide toward an intervertebral disk space defined between two vertebrae for at least one of instruments and intervertebral implants used in intervertebral procedures, a distal end of the shaft being positionable within the intervertebral disk space to distract the two vertebrae; and
an intervertebral implant including a pair of members, with a first member positioned along one of the pair of tracks and a second member positioned along the other of the pair of tracks, each of the first and second members having a protuberance securable to the intervertebral instrument that facilitates the movement of the respective member along one of the tracks;
wherein the distal end of the shaft includes a removable section disposed between the first and second members, the removable section being selectively removable from the shaft.

12. The intervertebral instrument and implant kit according to claim 11, wherein the first and second members are separable from the intervertebral instrument.

13. The intervertebral instrument and implant kit of claim 11, wherein at least one of the members defines at least one opening for the reception of bone graft or bone enhancers to enable bone ingrowth.

14. The intervertebral instrument and implant kit according to claim 11, further comprising a handle disposed at the proximal end of the shaft for manipulation of the shaft.

15. The intervertebral instrument and implant kit according to claim 11, wherein the removable section of the shaft, the first member, and the second member are collectively separable from the intervertebral instrument for collective implantation within a patient.

16. The intervertebral instrument and implant kit according to claim 11, wherein the removable section of the shaft includes a pair of wings for distracting the intervertebral disk space.

* * * * *